United States Patent [19]

Ophir

[11] Patent Number: 4,669,482
[45] Date of Patent: Jun. 2, 1987

[54] PULSE ECHO METHOD AND APPARATUS FOR SOUND VELOCITY ESTIMATION IN VIVO

[75] Inventor: Jonathan Ophir, Houston, Tex.

[73] Assignee: Board of Regents, The University of Texas System, Austin, Tex.

[21] Appl. No.: 791,719

[22] Filed: Oct. 28, 1985

[51] Int. Cl.[4] .............................................. A61B 10/00
[52] U.S. Cl. ..................................... 128/660; 73/597; 73/624; 73/626
[58] Field of Search ................................ 128/660–661; 73/597–598, 624–626

[56] References Cited

U.S. PATENT DOCUMENTS

| 4,105,018 | 8/1978 | Greenleaf et al. | 73/597 X |
|---|---|---|---|
| 4,202,215 | 5/1980 | Meyer | 73/599 |
| 4,210,028 | 7/1980 | Hildebrand | 73/598 |
| 4,286,455 | 9/1981 | Ophir et al. | 73/1 DV |
| 4,322,974 | 4/1982 | Abele et al. | 73/602 |
| 4,389,893 | 6/1983 | Ophir et al. | 73/599 |
| 4,406,153 | 9/1983 | Ophir et al. | 73/1 DV |
| 4,408,492 | 10/1983 | Kossoff et al. | 73/631 |
| 4,434,661 | 3/1984 | Miwa et al. | 73/625 |
| 4,452,081 | 6/1984 | Seppi | 128/660 X |
| 4,542,747 | 9/1985 | Zurinski et al. | 128/660 |
| 4,566,459 | 1/1986 | Umemura et al. | 128/660 |

OTHER PUBLICATIONS

"Measurement of Velocity of Propagation from Ultrasound Pulse-Echo Data" Robinson, et al., *Ultrasound in Med. & Biol.*, vol. 8, No. 4, pp. 413–420, 1982.

"Image Matching for Pulse Echo Measurement of Ultrasound Velocity" Robinson, et al., *Image and Vision Computing*, vol. 1, No. 3, pp. 145–151, 1983.

"Reconstruction of Ultrasound Propagation Speed..." Glover, et al., *IEEE Transactions on Sonics and Ultrasonics*, vol. SU-2, No. 4, Jul. 1977, pp. 229–234.

Proceedings of the 4th Annual Meeting of the World Federation of Ultrasound in Medicine and Biology, 1985, edited by J. P. Jones & S. Leeman, pp. 515–522.

*Primary Examiner*—Kyle L. Howell
*Attorney, Agent, or Firm*—Arnold, White & Durkee

[57] ABSTRACT

Sound velocity along a straight segment is estimated by measuring ultrasound pulse travel time as ultrasound pulses are directed along the straight segment from successively different transmitting or receiving positions. A sequence of data pairs comprising travel times and distances traveled is measured and plotted on a graph. Estimated sound velocity is derived from the slope of affine equation fitted to the plotted points.

19 Claims, 10 Drawing Figures

PULSE ECHO METHOD AND APPARATUS FOR SOUND VELOCITY ESTIMATION IN VIVO

BACKGROUND OF THE INVENTION

1. Field of the Invention

This invention relates generally to the use of ultrasound techniques for the measurement of sound velocity in organisms. More particularly, the invention relates to an apparatus and method for the estimation of sound velocity in medical diagnostics. The invention is especially concerned with measuring the travel time of ultrasonic pulses across known distances in the human body.

2. Background Art

X-ray diagnostic techniques, because of their increased toxicity to organic tissue, have been supplanted in many applications by ultrasound. Ultrasound has proved to be highly effective for producing images of the internal organs of the body. In addition, it has been found that certain pathological conditions in living organs cause changes in the velocity at which sound propagates in the organ. For example, cirrotic liver tissue is more dense than normal liver tissue. The velocity of sound in cirrotic tissue is therefore greater than that in normal tissue. Similarly, the increased tissue density in the region of tumors will result in an increased sound velocity in the tumor region. Measurement of sound velocity in the organ can thus be useful in the diagnosis of disease.

A simple method of sound velocity measurement involves the transmission of sound pulses through tissue regions of known dimension and recording of the time required for the pulse to traverse the region. The quotient of travel distance and travel time is computed to yield the velocity.

The transmission and reception of sound energy in medical diagnostics is accomplished with ultrasound transducers. These transducers contain piezoelectric crystals which produce an electric potential difference proportional to the amount by which they are physically deformed. Conversely, the application of an electric potential difference across the crystal causes a proportional physical deformation. As a consequence, the transducer may be used as both a transmitter and a receiver of ultrasound energy. An example of a practical embodiment of ultrasound transducers used in the medical field is described in an aritcle entitled "The U.I. Octoson—A New Class of Ultrasonic Echoscope" by Carpenter, et al., in *Australasian Radiology*, Vol. 21, No. 1 (1977) pp. 85–89.

These transducers are characterized by high directivity. In the transmit mode, a transducer will produce sound in a relatively narrow beam surrounding the transducer's axis of radiation. The transducer is correspondingly directional in the receive mode in that it will only respond to sound energy directed to it along a line nearly coincident to its axis of radiation.

One configuration that has been used in medical diagnostics requires a transmitting transducer and a separate receiving transducer arranged so that they are aimed at one another with their respective axes of radiation coincident. The body of the subject is placed between the transmitting and receiving transducers. Acoustical coupling may be accomplished in one of two ways. The subject may be required to stand immersed in a tank of water so that the water effects a coupling to the transducers. Alternatively, the transducers may be attached directly to the skin of the subject on either side of the body or an appendage thereof, and an acoustical coupling agent applied between the transducer and the skin to insure tight acoustical coupling.

The two-transducer configuration may be effective when used with body appendages, such as the breast or testes, where the transducers may be attached directly on either side of the organ of interest. Often, organs such as the liver are not so readily accessible. Use of the above recited configuration will require placement of transducers on opposite sides of the body and will require the ultrasound energy to traverse other organs and bone as well as the organ of interest. The quotient of distance and travel will thus yield a weighted average of the velocities in the various organs and bone traversed. In addition, refraction will occur at each tissue interface resulting in a bending of the path of the incident ultrasound pulse off the axis of radiation of the receiving transducer.

A second configuration that has been used in medical diagnostics is a modification of the first-described configuration in which a single transducer serves as both transmitter and receiver. A sound mirror, such as a steel plate, is placed in the position occupied by the receiving transducer in the first-described configuration and the transducer formerly used only for transmitting is now used also as a receiving transducer.

This second configuration does have a slight advantage over the first configuration in that only one transducer is required. However, the previously-described disadvantages still remain. Moreover, the sound pulse is now required to traverse the entire cross-section of the body twice, once as an incident wave, and a second time as a reflected wave. Consequently, attenuation of the pulse is doubled. The previously-recited problem with acoustical refraction is also exacerbated in that the pulse path must now undergo bending not only for the path of the incident wave, but for the path of the reflected wave as well.

A more sophisticated technique for sound velocity estimation is disclosed by Robinson, Chen and Wilson in "Image Matching for Pulse Echo Measurement of Ultrasound Velocity", published in *Image and Vision Computing*, Volume 1, Number 3, Aug., 1983. In this method, sound images of a tissue region are obtained from different angles. Sound velocity may be determined from the difference in position of the same feature in different images. This method works best when a well defined feature is available. In simulated tissue regions, known as "phantoms", a thin wire added to the region will provide such a well defined feature. Features normally appearing in living tissue are not as well defined and the resulting measurement is therefore not as accurate.

Accuracy in sound velocity estimation is extremely important in the analysis of tissue for pathological conditions. Using the liver as an example, sound velocity will be fairly uniform with variations due to both natural inhomogeneities and pathological conditions amounting to about 5%. Accuracy of estimation of velocity must be at least 0.5% provide adequate diagnosis of organ disease. Many factors affect the measurement accuracy, including the refraction occuring at the tissue interfaces, the limited accessibility of some organs, and the dispersive attenuation of ultrasound energy by the tissue itself. Sound velocity estimation in organic tissue requires a technique capable of overcoming these limitations while being relatively simple to implement and apply.

SUMMARY OF THE INVENTION

The invention takes advantage of the acoustical properties of organic tissue. The tissue contains a large number of "scatterers." These scatterers are inhomogeneities in the tissue which, being small compared to the wavelength of the sound frequencies involved, tend to reflect incident sound energy in all directions. Scatterers may be thought of as analogous to droplets of water vapor in fog which scatter and diffuse the light from automobile headlamps. The invention in a general aspect resides in a system in which pulses of ultrasonic energy are sent through a selected organism or portion of an organism. As an individual pulse passes between a transmitter and a receiver, its total travel time is noted. More importantly, as it passes along a straight line through a region of interest, its travel time along a plurality of segments of the straight line is also noted. From this information, the velocity of the sound through each of the segments can be determined. These data, in turn, are useful in identifying possible abnormalities or unusual conditions in the organism.

The high directivity of the ultrasound transducers as transmitters permits ultrasound energy to be directed in a relatively narrow beam toward selected points within the tissue. As receivers, the transducers receive energy within a narrow beam width, and may thus be aimed at specific points within the tissue. Transducers used in the medical ultrasound art are commercially available as individual transducer units, or packaged as a linear array of individual transducer elements. Transducer arrays may comprise as many as 200 individual transducer elements arranged side by side with their respective axes of radiation parallel. Spacing between these transducer elements within transducer arrays is typically about 1 millimeter.

The estimation of sound velocity in an organism begins by selecting a straight segment in an organism to lie along the axis of radiation of a transducer. The axis of either the transmitting transducer or the receiving transducer may be selected. For simplicity of description, it will be assumed that the straight segment lies along the axis of radiation of a transmitting transducer. Thus, a plurality of transducers may be so aimed as to receive scattered energy from spaced points along the straight segment as ultrasound pulses are transmitted. For each point from which scattered energy is received, the total travel time required for the pulse to be transmitted to the point, and for scattered energy to be received from that point is detected. Determined along with the travel time is a distance from the point to a reference point on the straight segment. The travel time together with the distance form one data pair.

The data pairs for each reflection point are fitted to an affine equation of the form $$T = AD + B$$

where
T = travel time
D = D distance to the reference point and
A and B are constants.

If the equation is plotted on rectangular time distance coordinates, A will be the slope of the equation and B will be the time axis intercept. A will have the dimensions of time divided by distance. The reciprocal of A, i.e., 1/A, will represent the estimated average velocity along the chosen straight segment.

Another aspect of the invention concerns a particular apparatus for carrying out the method of the invention. The apparatus comprises two separate linear arrays of transducers—one an array of transmitters, and the other, an array or receivers—joined at their proximal ends by the free ends of two arms which are pivotally connected at their other ends. The free end of each such arm is pivotally connected to the free end of one of the arrays, and the arms are preferably equal in length. Each array of transducers comprises a plurality of transducers arranged to transmit or receive, as the case may be, ultrasonic energy along parallel paths between the transducers and the echo points. This form of apparatus has ready application in medical diagnostics, where the two arrays may be placed directly on the body of a patient.

Another form of apparatus comprises transducers which rotate and transmit or receive at various rotational positions. Using this embodiment, a single transmitter can be synchronized with a single receiver such that the beams emitted by the transmitter reach echo points at the same time that the receiver is positioned to receive reflected energy from such echo points. By synchronizing both rotations, the echo points can be positioned along a straight line which penetrates an area of interest in an organism.

DESCRIPTION OF THE PREFERRED EMBODIMENT

In the present invention, transmitting means suitable for transmitting pulses of ultrasound into the body are preferably implemented by ultrasound transducers. Such transducers are commercially available either as individual units or in arrays of many transducer elements. Commercially available arrays may have as many as 200 transducer elements arranged linearly with a spacing of about one millimeter. An electrical pulse supplied to transducers of this type is internally applied to a piezoelectric crystal which is deformed responsive to the electrical pulse. The mechanical deformation of the crystal produces a pulse of ultrasound energy which is directed into the body. It will be obvious to those skilled in the art that any transmitting means embodiment capable of producing ultrasound pulses of pulse width or duration of approximately 0.25 microseconds to approximately 5 microseconds will be suitable for use in the present invention. Suitable transmitting means must further be capable of producing pulses of sufficient amplitude to overcome the levels of ultrasound attenuation encountered in organic tissue.

Receiving means suitable for receiving ultrasound energy scattered from points inside the tissue are preferably implemented by ultrasound transducers of the type disclosed above. Mechanical deformation of the piezoelectric crystal by received ultrasound pulses produces electrical pulses responsive to the deformation. The electrical pulse so produced may be amplified and observed by suitable observing means. Suitable receiving means must at least be sufficiently sensitive to respond to the amplitude levels of ultrasound energy scattered from points inside the tissue. Additionally, suitable receiving means must have sufficiently high frequency response to respond to ultrasound pulses of the short duration produced by the transmitting means.

The present invention further requires observing means suitable for observing both the transmitted ultrasound pulse as well as the received scattered energy pulse so as to measure the time interval between their respective occurrences. An example of suitable observing means is the cathode ray oscilloscope of a type ordinarily used in the electronic laboratory. An alternate embodiment of observing means would comprise an electronic counter started by the occurrence of the transmitted ultrasound pulse and stopped by the reception of the scattered energy pulse. At a minimum, suitable observing means must be capable of responding to pulses of the amplitude and duration supplied to the transmitting means as well as the pulses of amplitude and duration received by the receiving means. Additionally, suitable observing means must be capable of differentiating the received pulse from background noise and extraneous pulses. Finally, suitable receiving means must allow accurate measurement of the time interval between transmission of an ultrasound pulse and the received scattered energy pulse.

The level of accuracy required in the time observation will depend on the particular application. Velocity of sound in human organs is generally of the order of 1,500 meters per second. Many factors, such as the temperature of the organ tissue as well as the presence of disease, will cause variations in sound velocity. Generally, the variation of sound velocity in a particular organ will be of the order of 5% due to all causes. Hence measurement accuracy should be of the order of 0.5% or less for the velocity estimation to be useful.

Total distances traveled by ultrasound pulses in the human body will be of the order of ⅔ meter or less. Hence, the travel times to be measured will be of the order of 200 microseconds or less. Suitable observing means must be capable of measuring times of this order with an accuracy of ±1.0 microsecond or less. The typical oscilloscope used in electronic laboratories having the capability of measuring time intervals with an accuracy of plus or minus a few nanoseconds ($10^{-9}$ second is seen to be one embodiment of a suitable observing means.

Although disclosed within the context of velocity estimation in human tissue, the present invention will be equally applicable to velocity estimations in the organs of the lower animals. Additionally, the present invention may be used in inorganic media as well. The present invention may be used to estimate sound velocity in any medium having the acoustical scattering properties described herein. In media other than organic tissue, the sound velocities encountered and the percentage variations thereof will dictate other error criteria. These error criteria will place corresponding constants on the parameters of the observing means.

Figure 1:
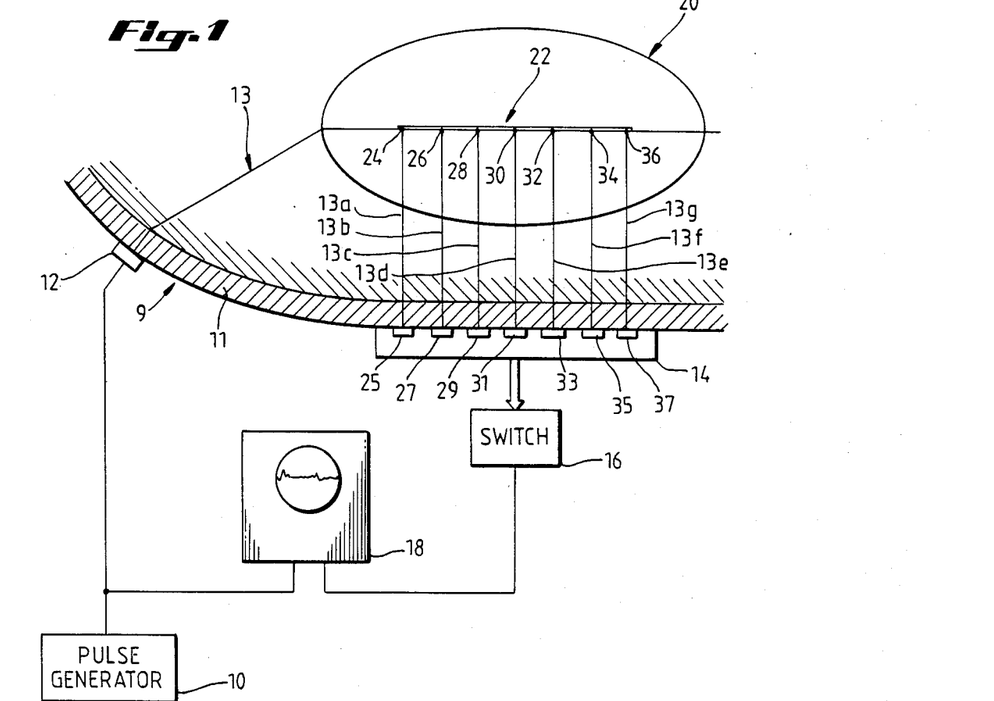
FIG. 1 shows one embodiment of the apparatus used for sound velocity estimation wherein a single transmitting transducer and a receiving transducer array are used.

Referring now to FIG. 1, an embodiment of the invention is shown wherein a single transmitting transducer 12 and a receiving transducer array 14 are used to estimate the velocity of sound along the straight segment 22. Pulse generator 10 produces an electrical pulse with a duration between about 0.25 microseconds and about 5 microseconds to transducer 12. Transducer 12 is attached to the surface of the skin 9 and emits an ultrasound pulse which travels along path 13 through the fat layer 11 and further travels along straight segment 22 in the region of interest 20. Region 20 may be a particular organ in the body. Ultrasound energy scattered from reflection points along straight segment 22 may be received by transducer elements within transducer array 14. The outputs of the transducer elements 25, 27, 29, 31, 33, 35 and 37 are conducted into switch 16 where one of the outputs is selected to be conducted into oscilloscope 18. FIG. 1 shows 7 transducer elements for simplicity of illustration.

Initially, the output of element 25 is selected by switch 16 to be conducted to and displayed by oscilloscope 18. An incident pulse emitted from transducer 12 is displayed at 48 in FIG. 2 on trace 42 on oscilloscope screen 40. The incident pulse travels along path 13 to reflection point 24 and some of the energy of the incident pulse is scattered along path 13a to transducer element 25 of array 14. The energy received by element 25 is shown at 50 on trace 44 in FIG. 2. Element 25 receives scattered energy from scatterers surrounding point 24, hence the trace shows several jagged peaks at 50. The time $T_1$ is measured from the highest peak of the pulse 48 to the highest peak of the pulse 50. The travel time $T_1$ could also have been measured to the centroid of the scattered energy pulse 50. That is, expressing the scattered energy pulse 50 as a function of time f(t), the centroid occurs at a point Tc such that $$Tc = \frac{\int f(t)\, t\, dt}{\int f(t)\, dt}$$

The time $T_1$ must be paired with a distance to form a data pair corresponding to the point 24. A reference point is selected on the straight segment 22 and the distance from reflection point 24 to the reference point is recorded along with time $T_1$ to form the data pair corresponding to reflection point 24. Any point on straight segment 22 may be selected as a reference point. The reference point may, for convenience, be one of the reflection points 24, 26, 28, 30, 32, 34 or 36. If point 24 is selected as the reference point, the distance recorded along with $T_1$ would be 0.

Figure 2:
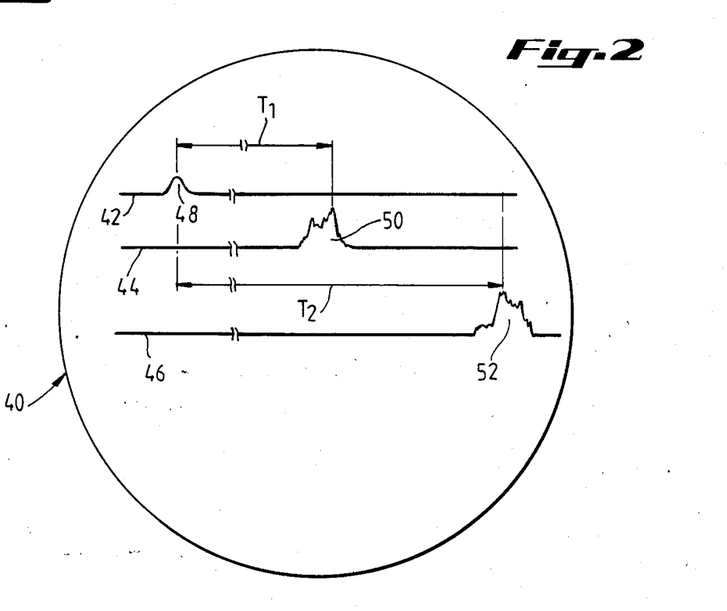
FIG. 2 shows typical oscilloscope traces of incident and scattered energy pulses observed during the measurement process.

Data pairs are collected for each of the remaining reflection points 26 through 36 shown in FIG. 1 in a similar manner. Referring now to FIG. 2, trace 46 shows the scattered energy pulse 52 which would result from the transmission of pulse 48. Pulse 52 represents the energy scattered from reflection point 26 to be received by element 27. A time $T_2$ elapses between the transmission of pulse 48 and the reception of pulse 52 by transducer element 27. Switch 16 is used to select transducer element 27 for reception. If reflection point 24 is selected as the reference point, the distance recorded along with time $T_2$, corresponding to point 26, is a spacing D between the points 24 and 26. Assuming that refraction equally affects energy passing to each of the transducer elements of array 14, D is just the spacing between the transducer elements of array 14. For the configuration of FIG. 1, a total of 7 data pairs would be collected. Using point 24 as the reference point, the distances recorded for each reflection point would be as follows:

| Point | Distance Recorded |
| --- | --- |
| 24 | 0 |
| 26 | D |
| 28 | 2D |
| 30 | 3D |
| 32 | 4D |
| 34 | 5D |
| 36 | 6D |

If another reflection point was selected as the reference point, different distances would be recorded. For example, suppose reflection point 30 is so chosen. Then, the distances recorded would be as follows:

| Point | Distance Recorded |
| --- | --- |
| 24 | −3D |
| 26 | −2D |
| 28 | −D |
| 30 | 0 |
| 32 | D |
| 34 | 2D |
| 36 | 3D |

The travel times would be the same irrespective of the distances used. The change in reference point merely changes the intercept of the affine equation to be fitted but does not change its slope. As previously disclosed, it is the slope of the affine equation which is of interest in the present invention.

The foregoing description of the measurement technique has omitted the complication that a sequence of pulses must be emitted by the pulse generator and a sequence of scattered energy pulses must be received in order for the conventional oscilloscope to provide a persistent display. Alternatively, a storage type oscilloscope may be used wherein the screen 40 is adapted to store a single trace without the need for pulse repetition. As a further alternative, observing means other than an oscilloscope may be used so long as these observing means are capable of detecting the occurrence of the scattered energy pulses and measuring the time between their arrival to the respective transducer elements 25 through 37. Utilizing such alternative means, a single pulse could be emitted from transducer 12 and the occurrence of scattered energy pulses from points 24 through 36 recorded. Then the sequence of times between successively received scattered energy pulses could be recorded along with the distances between adjacent points to comprise the complete set of data pairs.

Figure 3:
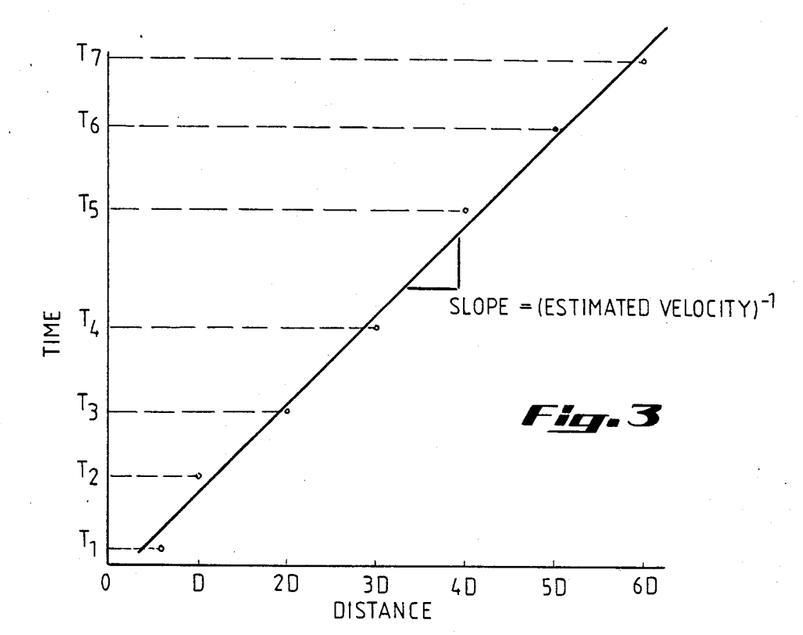
FIG. 3 shows a graph whereon data pairs are plotted and an affine equation is fitted to the plotted points.

Referring now to FIG. 3, a plot of the seven data pairs is shown. A straight line is fitted to the data points, using the least squares method. The slope of the line has the dimensions of time divided by distance, and the reciprocal of the slope is the estimated velocity of sound along the straight segment 22. While a graphical illustration is used for clarity of understanding, the fitting of the data pairs need not require the drawing of the graph.

Let the N data pairs collected be represented as (Di, Ti), where each Di is a distance and each Ti is a travel time. The affine equation $T=AD+B$ may be fitted to the data pairs by selecting the constants A and B to minimize the least squares error:

$$E = \sum_{i=1}^{N} (Ti - A\,Di)^2$$

The affine equation plotted on the time vs. distance coordinates will result in a straight line having an intercept on the time axis equal to B and a slope of A. The slope A, having the units of time divided by distance, will be the reciprocal of the average value of the velocity of sound along the transmitting transducer's axis in the region of interest.

Figure 4:
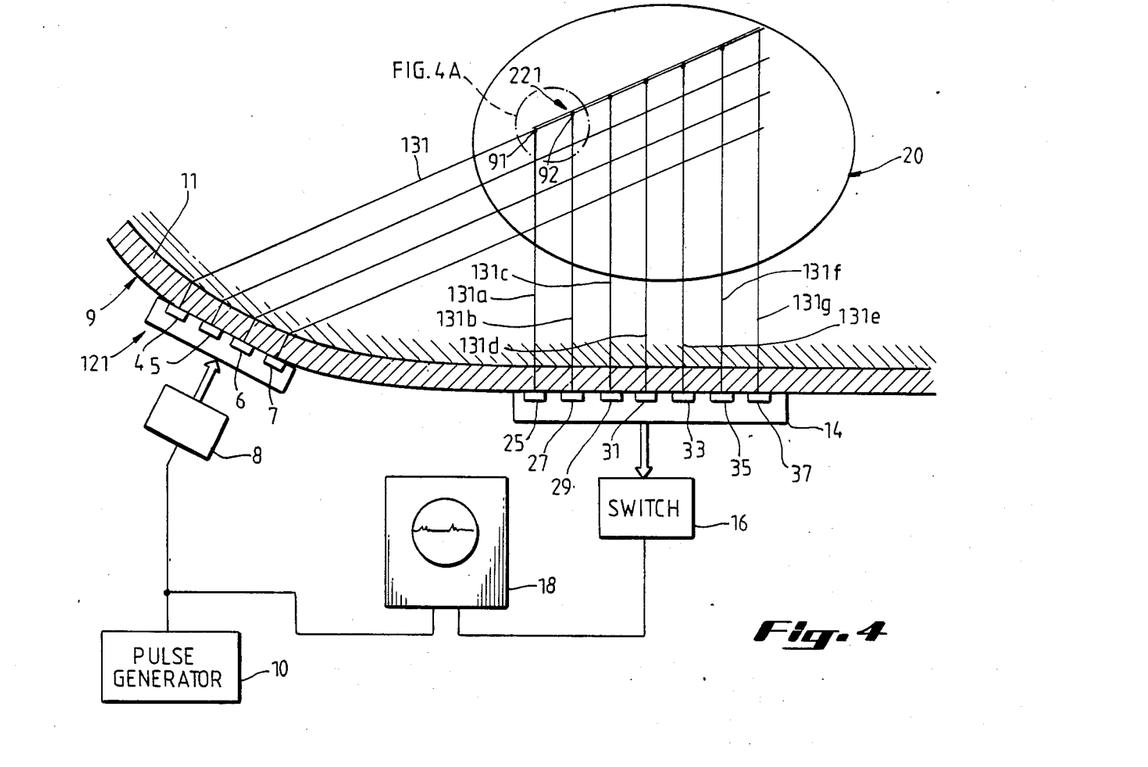
FIG. 4 shows an alternative embodiment of the measurement apparatus wherein transducer arrays are used for transmitting and receiving ultrasound.

Referring now to FIG. 4, a more complex transducer configuration is depicted. Single transducer 12 used in the configuration of FIG. 1 has been replaced by the transducer array 121 in FIG. 4. Transducer array 121 comprises transducer elements 4, 5, 6 and 7. Although only four transducer elements are shown for simplicity, a larger number could be used. The pulse conducted from pulse generator 10 is switched to one of the four elements of array 121 by switch 8. Thus, the velocity of sound may be estimated along several straight segments like that of straight segment 22 of FIG. 1 without the necessity of moving array 121 to a new position on the surface of the body. Additionally, elements of the receiving transducer array 14 will receive energy scattered from points at an angle other than 90°, thus requiring a correction to be made in the travel time measurement.

The correction is illustrated by estimations made of the velocity of sound along straight segment 221 in FIG. 4. A pulse emitted from element 4 of array 121 traverses path 131 and is scattered from point 91 along path 131a to element 25 of array 14. Subsequently, a second pulse is emitted from element 4 which traverses path 131 and is scattered from point 92 along path 131b to element 27 of array 14. Note that while paths 13a and 13b in FIG. 1 are essentially equal in length, paths 131a and 131b in FIG. 4 are not. Thus, in the configuration of FIG. 4, the difference in travel time from element 4 to point 91 to element 25, and the travel time from element 4 to point 92 to element 27, is not equal to the travel time from point 91 to point 92.

Figure 4A:
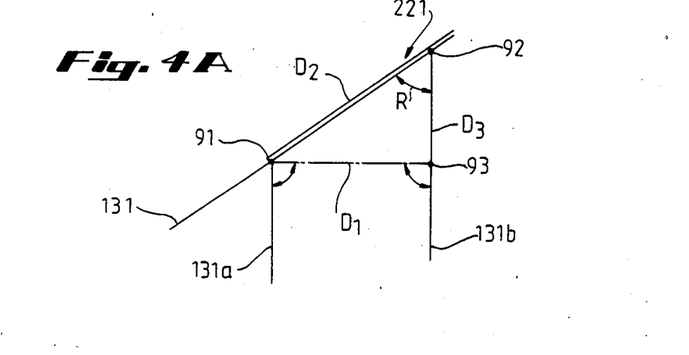
FIG. 4A shows an enlargement of a part of FIG. 5 wherein time and distance corrections are illustrated.

First, a distance correction is made wherein the effects of refraction are ignored. That is, it is first assumed that paths traveled by ultrasound pulses will not be bent by tissue interfaces and hence will follow the axis of radiation of the transducers. The assumption is thus made that point 91 lies at the intersection of the axes of radiation of elements 4 and 25. Similarly, it will be assumed that point 92 will lie at the intersection of the axes of radiation of elements 4 and 27. FIG. 4A is an enlargement of the region near points 91 and 92 showing a point 93 on path 131b. The distance $D_1$ is equal to the spacing between elements in array 16. The angle R is the angle of intersection of the axes of the transmitting and receiving elements. R is derivable from the known and measurable physical positions of the arrays 121 and 14.

Let $T_1$ be the travel time from element 4 to point 91, thence to element 25. Assuming point 91 to be the reference point, the first data pair will comprise the time $T_1$ and the distance 0. Further, let $T_2$ be the measured travel time from element 4 to point 92, thence to element 27. The time $T_2$ will be corrected to account for the additional length $D_3$ of path 131b. The distance $D_2$ between point 91 and point 92 will be calculated as a first step in the correction process.

By an obvious trigonometric calculation, from FIG. 4A, $D_3$ is:

$$D_3 = D_2 \cos R$$

Additionally, the distance $D_2$ is $$D_2 = \frac{D_1}{\sin R}$$

The time $T = (T_2 - T_1)$ is just the travel time along straight segment 221 from point 91 to point 92, plus the travel time along path 131b from point 92 to point 93. Letting Ta be the travel time from point 92 to point 93, $$\frac{Ta}{T} = \frac{D_3}{D_2 + D_3} = \frac{\cos R}{1 + \cos R}$$

The corrected value of $T_2$, call it $T_2'$, is $(T_2 - Ta)$. Hence $$T_2' = T_2 - \frac{T \cos R}{(1 + \cos R)}$$

The data pair corresponding to point 92 now comprises the corrected time $T_2'$ together with the distance $$D_2 = \frac{D_1}{\sin R}$$

Note that when $R = 90°$, $T_2' = T_2$ and $D_2 = D_1$. Hence applying the correction procedure when $R = 90°$ no change to the value of the numbers in data pairs.

Figures 5, 5A:
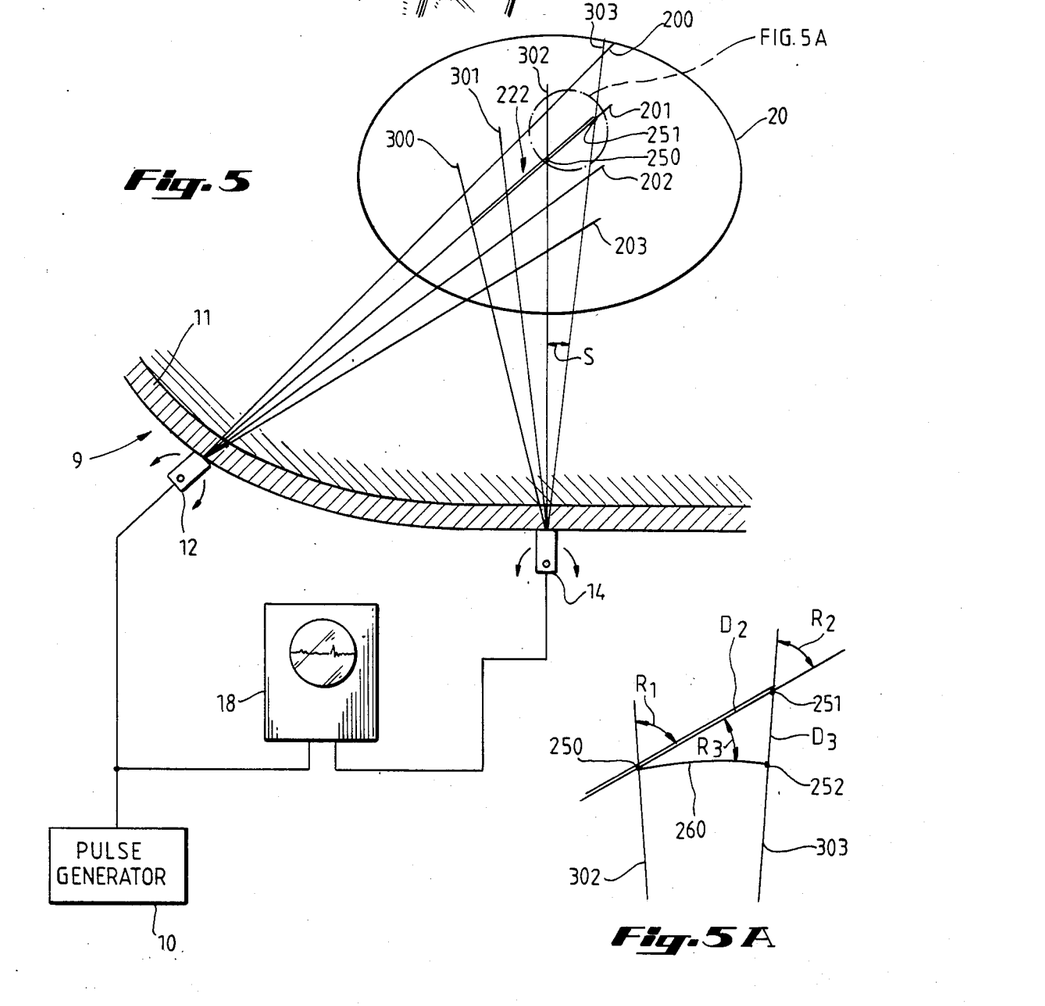
FIG. 5 shows an alternative embodiment of the measurement apparatus wherein a single transmitting transducer and a single receiving transducer are used.
FIG. 5A shows an enlargement of a part of FIG. 5 wherein time and distance corrections are illustrated.

Referring now to FIG. 5, a configuration is employed wherein transmitting transducer 12 and receiving transducer 141 are each rotatable about an axis perpendicular to the straight segment as shown but are held in a fixed location. Thus, the paths along which pulses are emitted by the single transducer 12, and along which scattered energy is received by the single transducer 14 are continuously selectable over a range of angles. Shown are 4 possible transmitting paths 200, 201, 202 and 203, as well as 4 possible receiving paths 300, 301, 302 and 303. An illustrative straight segment 222 is shown along path 201. Since the transmitting and receiving paths in general will not intersect at angles of 90°, corrections analogous in an obvious way to that disclosed for the configuration of FIG. 4 must be made.

The single rotating transmitting and receiving transducer of FIG. 5 may be replaced by steerable phased arrays of a type well known and used for radar and sonar. Such steerable arrays for ultrasound may be implemented using linear arrays of nondirectional ultrasound transducer elements. The steering is accomplished using variable delay elements in conjunction with the nondirectional transducer elements.

A steerable transmitting array would be implemented by supplying a single electrical pulse through individual delay elements to each of the nondirectional transducer elements. The delay elements are adjusted so that the nondirectional energy emitted from the transducer elements reinforce in a chosen direction. Similarly, the electrical output of nondirectional receiving transducer elements are fed through individual variable delay elements and added together before being fed to the observing means. Adjustment of the variable delay elements will cause the receiving array to be sensitive only to ultrasound received along a single resulting direction. Adjustment of the delay elements in a manner well known in the radar and sonar art has the effect of moving the axis of radiation of the transmitting and/or receiving array without requiring actual physical rotation.

The correction of travel times and distances for the configuration of FIG. 5 is better understood by reference to FIG. 5A, in comparison to FIG. 4A. The difference in travel time measured in the configuration of FIGS. 5 and 5A will be the time required for ultrasound energy to travel a distance $D_2$ from point 250 to point 251 plus a time required to travel a distance $D_3$ from point 251 to 252. Points 250 and 252 lie on arc 260 and are equidistant from transducer 14. For a small angle S, arc 260 will be nearly a straight line intersecting path 302 at an angle approximately equal to 90°. Thus, for values of S less than about 5°, the correction, is made in a manner identical to that above disclosed.

The above disclosed correction process was based on the angle R being less than 90°. Further, in the configuration shown in FIGS. 4 and 4A, the reference point selected was the point closest to the transmitting array 121. The modification of the correction process to account for R being greater than 90° and for the selection of other reference points will be obvious so long as general nature of the correction is understood. Specifically, a distance correction is required so as to determine the true distance from a reflection point to a reference point on the straight segment. That distance will not be an integral multiple of the distance between transducer elements when R is other than 90° or if reference point is not a reflection point. Additionally, when the respective paths to the transducer elements whose axes intersect the straight segment are not equal in length, travel times associated with adjacent reflection points differ by an amount which is greater than the time required by ultrasound to travel between those points. A given travel time must thus be corrected by subtracting out this additional increment of time in a manner obviously analogous to that disclosed above.

In order to effect the corrections previously disclosed, some means of mechanically positioning and aiming transducers and transducer arrays is required. It will be obvious to one skilled in the mechanical art that many possible embodiments of such positioning means are possible. At a minimum, suitable positioning means would allow great flexibility in the placement of transducers on the surface of the body, and would further be able to sense and indicate the angle of intersection of the axes of the transmitting and receiving transducer elements.

Figure 7:
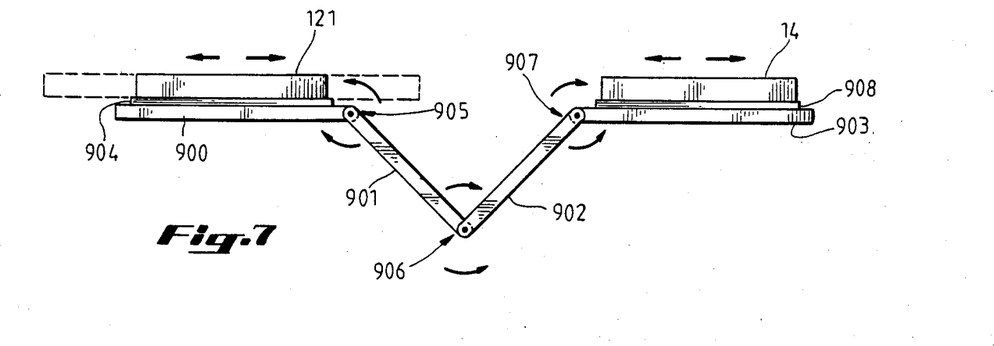
FIG. 7 shows representative positioning means suitable for positioning the transducers used in the measurement apparatus.

FIG. 7 depicts a simple but workable embodiment of suitable positioning means. More advanced embodiments will be obvious to those skilled in mechanical design. The embodiment of FIG. 7 illustrates the characteristics required for suitable positioning means. Arm 900 is pivotally connected to arm 901 allowing rotation in a plane. Angle sensor 905 senses the angle between arms 900 and 901. Arm 901 is similarly pivotally connected to arm 902 with angle sensor 906 sensing the angle between arms 901 and 902. Finally, arm 902 is pivotally connected to arm 903, with angle sensor 907 sensing the angle of intersection between arms 902 and 903. The pivotal mountings constrain arms 900, 901, 902 and 903 to lie in the same plane. By adjusting the relative positions of arms 900, 901, 902 and 903, the axes of radiation of the transducer elements in array 14 may be made to intersect the axes of radiation of the elements of the array 121.

Figure 7A:
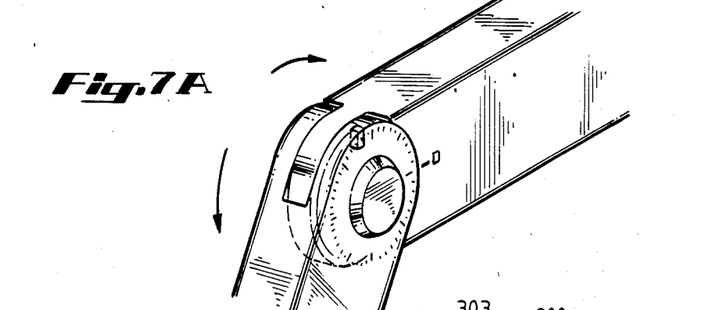
FIG. 7A shows one implementation of angle sensors employed in the positioning means embodiment of FIG. 7.

In a simple embodiment, angle sensors 905, 906 and 907 may be merely indicator dials by which the user may visually read the respective angles. An example of such an angle sensor embodiment is more particularly shown in FIG. 7A. In a more complex embodiment, these angle sensors may sense the respective angles electrically and produce an electrical representation of the respective angles to an electronic display or to a digital computer. Angle sensors of this type are well known to those skilled in the art of servomechanisms.

Array 121 is slidingly mounted on track 904, which is in turn rigidly mounted to and aligned with arm 900. In a similar fashion, array 14 is slidingly mounted on track 908, which is in turn rigidly mounted to and aligned with arm 903. This mechanical arrangement forces the axes of radiation of the elements of array 121 to intersect the axes of radiation of array 14 so that all intersection points lie in the same plane. Thus, given the lengths of the arms 900, 901, 902 and 903, the positions of arrays 121 and 14 on tracks 904 and 908 respectively, and the angles sensed by sensors 905, 906 and 907, the locations of intersection points of the radiation axes of the arrays 121 and 14 can be determined. Also, the angles of intersection of the axes of radiation are determinable by an obvious geometrical calculation. Finally, the mechanical arrangement of the positioning means of FIG. 7 allows placement of the arrays 121 and 14 at desired points on the surface of the body.

Figure 6:
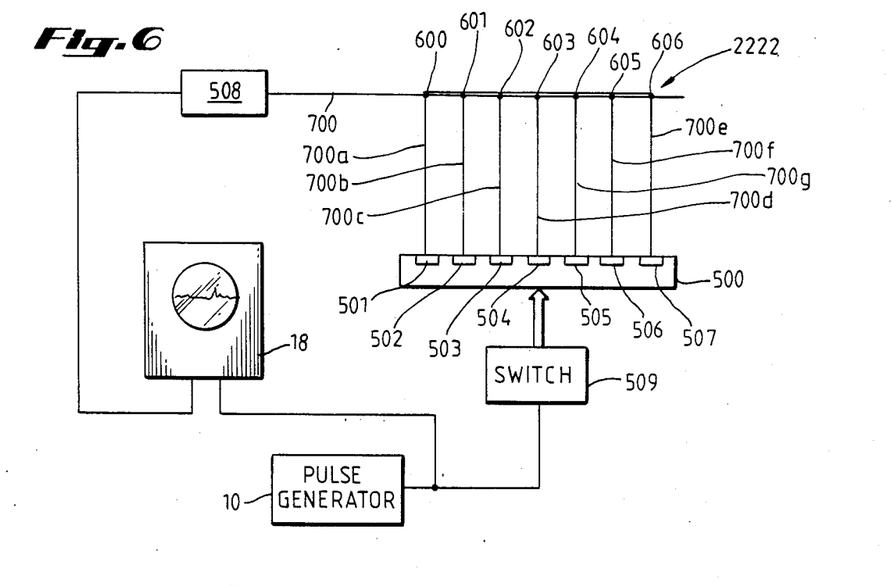
FIG. 6 shows an alternative embodiment of the measurement apparatus wherein the straight segment is selected to lie along the path of scattered energy traveling toward the receiving transducer.

The foregoing detailed disclosure of the invention has been directed to configurations wherein straight segments were selected to lie along paths of incident ultrasound pulses transmitted from transmitting transducers. Measurement segments may equally well be selected to lie along paths traversed by scattered energy pulses traveling toward receiving transducers, as illustrated by straight segment 2222 in FIG. 6. An electrical pulse from pulse generator 10 is selectably switched by switch 509 first to transducer element 501 of array 500. Element 501 emits a pulse of ultrasound energy along path 700a to point 600 and ultrasound energy is scattered from point 600 along path 700 to receiving transducer 508. A second electrical pulse from pulse generator 10 is switched by switch 509 to element 502. In response thereto, an ultrasound pulse is emitted by element 502 along path 700b and scattered along path 700 to receiving transducer 508. In a manner like that disclosed for the configuration of FIG. 1, the first data pair, comprising the travel time from element 501 to point 600 thence to element 508, and the distance between points 600 and 601, is recorded. Data pairs are thus collected for points along the straight segment 2222 and plotted as previously disclosed.

Although the invention is described by illustration of specific implementations, the details thereof are not to be considered limiting except to the extent of the following claims.

What is claimed is:

1. A method for estimating the velocity of sound along a straight segment within a region of interest in organic tissue, comprising the steps of:
   (a) measuring the travel time for a pulse of ultrasound energy to travel on a path extending from a transmitting ultrasound transducer to a receiving ultrasound transducer, said path traversing a portion of the straight segment between one end of said segment and a selected reflection point on said straight segment, one of said transducers being angulated with respect to said other transducer and spaced from said straight segment such that the portion of said path between said one transducer and said reflection point intersects said straight segment at said reflection point;
   (b) recording the travel time measured in step (a) together with the distance from said reflection point to a reference point on said straight segment to form a data pair;
   (c) repeating steps (a) and (b) for a plurality of other reflection points spaced apart on said straight segment to form a separate said data pair for each said other reflection point;
   (d) fitting the data pairs to an affine equation; and
   (e) deriving the estimated velocity of sound along said straight segment from the slope of said affine equation.

2. The method of claim 1, further comprising the step of correcting the travel time and distance so recorded for each said other reflection point for any difference in length between the path for said selected reflection point and said other reflection point other than the distance along said straight segment between the two reflection points.

3. The method of claim 1, wherein said step of fitting the data pairs to an affine equation comprises employing the least squares error criterion.

4. The method of claim 1, wherein said one transducer is said receiving transducer and further comprising the step of positioning said transmitting ultrasound transducer so that a pulse of ultrasound energy emitted therefrom travels substantially along said straight segment.

5. The method of claim 1, wherein said one transducer is said transmitting transducer, further comprising the step of positioning said receiving ultrasound transducer to receive said ultrasound energy scattered substantially along said straight segment.

6. A method of estimating the velocity of sound along a straight segment within a region of interest in organic tissue, comprising the steps of:
   (a) selecting a reference point on said straight segment;
   (b) selecting a reflection point on said straight segment;
   (c) positioning a transmitting ultrasound transducer so as to transmit a pulse of ultrasound energy substantially along said straight segment;

(d) positioning a receiving ultrasound transducer at an angle with respect to said transmitting transducer so as to receive energy from said pulse scattered from said reflection point;

(e) measuring a travel time required for a pulse of ultrasound sound energy to travel from the transmitting ultrasound transducer to the receiving ultrasound transducer along a path associated with said reflection point, said path extending along a portion of said straight segment and including said reflection point;

(f) recording the travel time measured in step (e) together with the distance from said reflection point to the reference point to form a data pair;

(g) repeating steps (b) through (f) for a plurality of other reflection points spaced apart on said straight segment to form a separate said data pair for each said other reflection point;

(h) fitting said data pairs to an affine equation; and (i) deriving the estimated velocity of sound along the straight segment from the slope of the affine equation.

7. A method of estimating the velocity of sound along a straight segment within a region of interest in organic tissue, comprising the steps of:

(a) selecting a reference point on said straight segment;

(b) selecting a reflection point on said straight segment;

(c) positioning a transmitting ultrasound transducer spaced from said straight segment so as to transmit a pulse of ultrasound energy to the reflection point;

(d) positioning a receiving ultrasound transducer at an angle with respect to said transmitting transducer so as to receive energy from said pulse scattered from said reflection point along said straight segment;

(e) measuring a travel time required for a pulse of ultrasound energy to travel from the transmitting ultrasound transducer to the receiving ultrasound transducer along a path associated with that reflection point, said path extending along said straight segment and including said reflection point;

(f) recording the travel time measured in step (e) together with the distance from said reflection point to said reference point to form a data pair;

(g) repeating steps (b) through (f) for a plurality of other reflection points spaced apart on said straight segment to form a separate data pair for each said other reflection point;

(h) fitting said data pairs to an affine equation; and (i) deriving the estimated velocity of sound along said straight segment from the slope of said affine equation.

8. The method of claim 6 or claim 7, further comprising the step of correcting the travel time and distance so recorded for each said other reflection point for any difference in length between the respective paths for said selected reference point and said other reflection point other than the distance along said straight segment between said two reflection points.

9. An apparatus for estimating the velocity of sound along a straight segment in a region of interest in organic tissue, comprising:

(a) transmitting means for transmitting pulses of ultrasound to a plurality of reflection points on the straight segment;

(b) receiving means for receiving ultrasound energy scattered from said reflection points said receiving means being angulated with respect to said transmitting means;

(c) positioning means for positioning said transmitting and receiving means; and (d) means for detecting the travel time required for a pulse of ultrasound energy to travel from said transmitting means to each said reflection point and be scattered therefrom to said receiving means.

10. The apparatus of claim 9, wherein said transmitting means comprises a linear array of ultrasound transducer elements arranged to transmit sound along parallel paths.

11. The apparatus of claim 9, wherein said receiving means comprises a linear array of ultrasound transducer elements arranged to receive sound along parallel paths.

12. The apparatus of claim 10 or claim 11, further comprising switching means adapted to selectively activate one of the ultrasound transducer elements of said array.

13. The apparatus of claim 10 or claim 11, wherein said arrays of ultrasound transducer elements are steerable phased arrays.

14. The apparatus of claim 9, wherein said transmitting means comprises a single ultrasound transducer held in a fixed location and rotatable about an axis perpendicular to the straight segment.

15. The apparatus of claim 9, wherein said receiving means comprises a single ultrasound transducer held in a fixed location and rotatable about an axis perpendicular to the straight segment.

16. An apparatus for estimating the velocity of sound along parallel straight segments in a region of interest in organic tissue, comprising:

(a) an electronic pulse generator adapted to produce an output of electronic pulses of a duration of between about 0.25 microseconds to about 5 microseconds;

(b) a linear array of transmitting ultrasound transducers adapted to transmit pulses of ultrasound in parallel paths, each said transmitting transducer positioned to send respective said pulses to a plurality of reflection points spaced along a separate one of said straight segments;

(c) transmitting switching means adapted to connect a selected said transducer of said array of transmitting ultrasound transducers to the output of the electronic pulse generator;

(d) a linear array of receiving ultrasound transducers adapted to receive ultrasound energy scattered along parallel paths from said reflection points responsive to pulses of ultrasound energy transmitted to said reflection points by said array of transmitting transducers, each said receiving ultrasound transducer having an electronic output;

(e) receiving switching means adapted to select the output of each one of said receiving ultrasound transducers;

(f) observing means adapted to observe the output of the receiving transducer selected by said receiving switching means, said observing means further adapted to observe the output of the electronic pulse generator; and (g) positioning means adapted to position both of said arrays.

17. The apparatus of claim 16, wherein said electronic pulse generator emitting an electronic pulse at a time $T_1$ to the transducer selected by said tranmitting switching means, said selected transducer transmitting a pulse of ultrasound energy to a reflection point on said straight segment, the ultrasound energy scattered from said reflection point arriving at the receiving transducer selected by said receiving switching means whereby an electronic pulse is produced at the output of said selected receiving transducer at a time $T_2$, said observing means adapted to display the time interval between $T_1$ and $T_2$.

18. The apparatus of claim 16 or claim 17, wherein said observing means comprises a cathode ray oscilloscope.

19. An apparatus for use in determining the velocity of sound in a position of the human body which comprises:

(a) a first linear array of transmitting acoustic transducers aligned to transmit parallel sound beams;

a second linear array of receiving acoustic transducers aligned to receive parallel sound beams;

(c) first and second arms pivotally connected at proximal ends to pivot about a first axis;

(d) said first arm pivotally connected at its distal end to a first end of said first linear array to pivot about an axis parallel to said first axis and normal to plane of the sound beams transmitted by said first array; and (e) said second arm pivotally connected at its distal end to a first end of said second linear array to pivot about an axis parallel to said first axis and normal to the plane of the sound beams received by said second array.

* * * * *